(12) United States Patent
Lin et al.

(10) Patent No.: US 8,691,796 B2
(45) Date of Patent: Apr. 8, 2014

(54) PHARMACEUTICAL COMPOSITION AND METHOD FOR INHIBITING INFLAMMATION

(75) Inventors: Feng-Huei Lin, Taichung (TW); Teng-Le Huang, Taichung (TW); Horng-Chaung Hsu, Taichung (TW)

(73) Assignee: China Medical University, Taichung (TW)

( * ) Notice: Subject to any disclaimer, the term of this patent is extended or adjusted under 35 U.S.C. 154(b) by 298 days.

(21) Appl. No.: 13/024,764

(22) Filed: Feb. 10, 2011

(65) Prior Publication Data

US 2012/0108536 A1      May 3, 2012

(30) Foreign Application Priority Data

Oct. 29, 2010   (TW) ................................ 99137186 A

(51) Int. Cl.
   *A61K 31/7008*   (2006.01)

(52) U.S. Cl.
   USPC ................................ 514/62; 514/53; 514/825

(58) Field of Classification Search
   CPC .................................................. A61K 31/7008
   USPC ............................................. 514/62, 53, 825
   See application file for complete search history.

(56) References Cited

U.S. PATENT DOCUMENTS 5,095,037 A * 3/1992 Iwamitsu et al. ............. 514/561
2004/0048910 A1  3/2004 Bove et al.
2007/0003636 A1  1/2007 Mach

FOREIGN PATENT DOCUMENTS

CN      1829501 A       9/2006
TW      200410677       7/2004
WO      WO 0137876 A2 * 5/2001
WO      2004/105737 A2  12/2004

OTHER PUBLICATIONS

European Search Report of Application No. 11181939.7 mailed Feb. 9, 2012.
Akasaki, Y et al., Mevastatin reduces cartilage degradation in rabbit experimental osteoarthritis through inhibition of synovial inflammation, Osteoarthritis and Cartilage, vol. 17, No. 2, Feb. 1, 2009, pp. 235-243.
Leopold, S et al., Increased frequency of acute local reaction to intra-articular hylan GF-20 (Synvisc) in patients receiving more than one course of treatment. J Bone Joint Surg, 2002;84: 1619-23.
Bernardeau, C et al., Acute arthritis after intra-articular hyaluronate injection: onset of effusions without crystal. Ann Rheum Dis, 2001;60:518-20.
Kroesen, S et al., Induction of an acute attack of calcium pyrophosphate dihydrate arthritis by intra-articular injection of hylan G-F 20 (Synvisc). Clin Rheumatol, 2000;19:147-9.
Homma, A et al., Novel hyaluronic acid-methotrexate conjugates for osteoarthritis treatment, Bioorganic and Medicinal Chemistry, 17 (2009), 4647-4656.
Taiwan Intellectual Property Office Action of Application No. 099137186 mailed Sep. 19, 2012.
"Intraarticular injection for rheumatoid arthritis," May 20, 2010, pp. 450-454.
Barrios-Gonzalez et al., "Biotechnological production and applications of statins," Applied Microbiology and Biotechnology, Jan. 2010, pp. 869-883, vol. 85—No. 4.
The Application of Sodium Hyaluronate in Joint Diseases, Chinese J. Reparative and Reconstructive Surgery, 2002, vol. 16, No. 1.

* cited by examiner

*Primary Examiner* — Patrick Lewis
*Assistant Examiner* — Everett White
(74) *Attorney, Agent, or Firm* — Ping Wang; Andrews Kurth LLP

(57) ABSTRACT

A pharmaceutical composition for inhibiting inflammation, comprising (a) hyaluronic acid, (b) a 3-hydroxy-3-methyl-glutaryl-coenzyme A (HMG-CoA) reductase inhibitor, and (c) a pharmaceutically acceptable carrier, is provided. Also provided is a method for inhibiting inflammation in a mammal, comprising administrating to the mammal an effective amount of a composition comprising (a) hyaluronic acid and (b) an HMG-CoA reductase inhibitor.

14 Claims, 1 Drawing Sheet

PHARMACEUTICAL COMPOSITION AND METHOD FOR INHIBITING INFLAMMATION

This application claims priority to Taiwan Patent Application No. 099137186 filed on Oct. 29, 2010.

FIELD

The present invention relates to a pharmaceutical composition for inhibiting inflammation, especially to a pharmaceutical composition useful for arthritis.

BACKGROUND

Arthritis is a common chronic disease, which leads to joint pain due to the degeneration of joint cartilage or the inflammation of connective tissue, and further influences the normal movement of the joint. According to the position and cause of the occurrence, arthritis can be classified into more than one-hundred types. The most common types include osteoarthritis (degenerative arthritis), rheumatoid arthritis (RA), gouty arthritis, bacterial arthritis, ankylosing spondylitis, lupus erythmatosus, etc.

Generally, in the treatment of arthritis, a conservative, non-surgical treatment is initially adopted. When the initial treatment is ineffective, a surgical treatment is then applied. The initial treatment includes drug therapy and injection therapy. In drug therapy, steroidal and non-steroidal anti-inflammatory agents are used. Although the pain-relieving effect of the steroidal agents is prompt and obvious, they may cause many side effects, such as osteoporosis, uncicatrized wounds, upper gastrointestinal bleeding, and may even aggravate existing conditions, such as hypertension, diabetes, etc. Thus, steroidal agents are currently used only in certain limited condition. As for non-steroidal agents, although they also have good pain-relieving activity, if used for a long-term period, side effects like peptic ulcer, lower limb hydrops, impairment of kidney function, etc., may arise. Hence, non-steroidal agents are restricted in practical application.

Hyaluronic acid injections have been broadly used in the treatment of osteoarthritis, in which an injection solution containing hyaluronic acid is directly injected into the joint to moderately alleviate inflammation and pain of patients. Although the mechanism of hyaluronic acid is still unclear, it is known that hyaluronic acid can serve as a lubricant to assist the joint movement and meanwhile improve the joint function. However, although hyaluronic acid may efficiently alleviate pain, it causes transient inflammatory reactions within two days to one week after entering the human body, and even leads to chronic inflammation (see Leopold et al., Increased frequency of acute local reaction to intra-articular hylan GF-20 (Synvisc) in patients receiving more than one course of treatment. *J Bone Joint Surg*, 2002; 84: 1619-23; Bernardeau et al Acute arthritis after intra-articular hyaluronate injection: onset of effusions without crystal. *Ann Rheum Dis*, 2001; 60:518-20; and Kroesen et al., Induction of an acute attack of calcium pyrophosphate dihydrate arthritis by intra-articular injection of hylan G-F 20 (Synvisc). *Clin Rheumatol*, 2000; 19:147-9, which are incorporated hereinto by reference). Thus, the anti-inflammation effect of the hyaluronic acid formulation products in the current market is not ideal.

A method for improving the hyaluronic acid formulation has been disclosed (see Homma et al., Novel hyaluronic acid-methotrexate conjugates for osteoarthritis treatment, Bioorganic and Medicinal Chemistry, 17 (2009), 4647-4656, which is incorporated hereinto by reference). In this method, hyaluronic acid is linked to methotrexate (MTX) with anti-inflammation activity via a polypeptide to form a conjugate using a chemical synthesis approach, and the resultant product has an improved anti-inflammation effect. Nevertheless, according to the disclosure of this document, a mixture formed by simply mixing hyaluronic acid and MTX cannot provide the improving effect; in other words, the synthesis of the conjugate is necessary. However, the preparation of the conjugate needs the use of polypeptide materials and involves complicated synthesis steps, which must increase the cost for manufacturing a hyaluronic acid formulation. Thus, this method not only has difficulties in mass production, but also increases the economic burden of users, and is quite limited in the clinical application. Therefore, there is still a need in the market for a medicament or method that can efficiently improve the anti-inflammation activity of hyaluronic acid and is also simple and convenient in terms of the manufacturing process.

The present invention is a research achievement for the above demand. The inventors of the present invention found that a composition prepared by mixing a 3-hydroxy-3-methylglutaryl-coenzyme A (HMG-CoA) reductase inhibitor and hyaluronic acid may inhibit the transient inflammatory reactions caused by hyaluronic acid, and further improve the anti-inflammation effect of hyaluronic acid.

SUMMARY

The primary objective of this invention is to provide a pharmaceutical composition for inhibiting inflammation, comprising (a) hyaluronic acid, (b) a 3-hydroxy-3-methylglutaryl-coenzyme A (HMG-CoA) reductase inhibitor, and (c) a pharmaceutically acceptable carrier.

Another objective of this invention is to provide a method for inhibiting inflammation in a mammal, comprising administrating to the mammal an effective amount of a composition comprising hyaluronic acid and an HMG-CoA reductase inhibitor.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
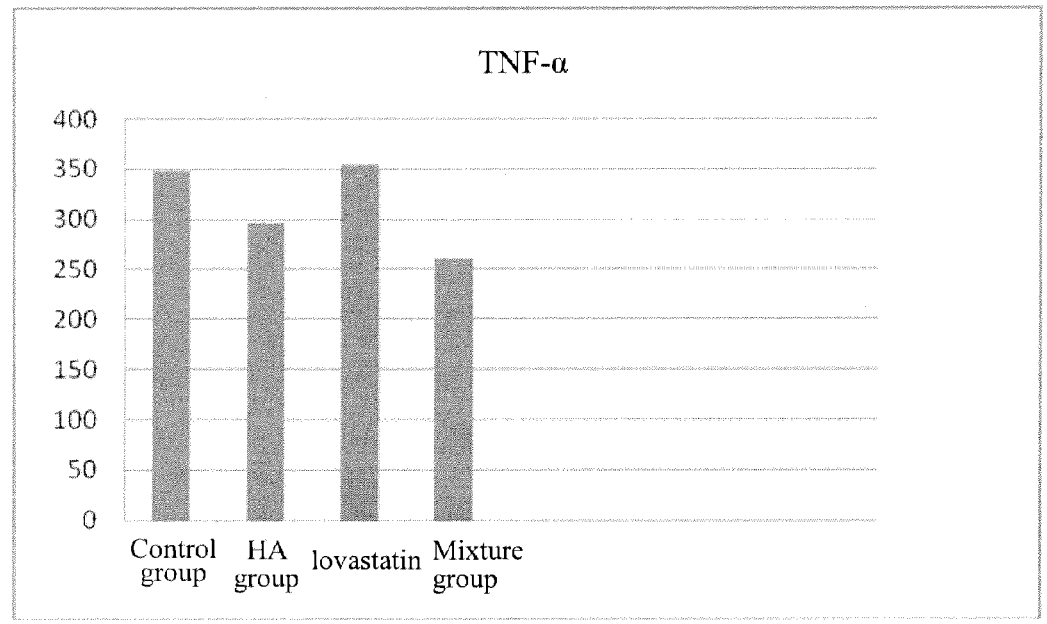
FIG. 1 is a statistical bar graph showing the expression level of the inflammatory mediator TNF-$\alpha$ in the Fibroblast-like synoviocytes (FLS)

Unless otherwise stated herein, the terms "a(an)", "the" or the like used in this specification (especially in the Claims hereinafter) shall be understood to encompass both the singular form and the plural form.

As stated above, hyaluronic acid may cause the transient inflammatory reactions within two days to one week after entering the human body, and even lead to chronic inflammation, thereby influencing the anti-inflammation effect thereof. On the other hand, the method by preparing the conjugate of hyaluronic acid and MTX has lots of limits. The present invention may improve the drawbacks of the conventional hyaluronic acid formulations with a simple approach by combining hyaluronic acid and a 3-hydroxy-3-methylglutaryl-coenzyme A (HMG-CoA) reductase inhibitor.

Therefore, the present invention provides a pharmaceutical composition for inhibiting inflammation, comprising (a) hyaluronic acid and (b) an HMG-CoA reductase inhibitor.

Hyaluronic acid is one of the major components constituting an extracellular matrix, and broadly exists in endothelial tissue, connective tissue, epidermal tissue, and nerve tissue, and is important to the physiological activity of cells, like proliferation, migration, etc. In addition, because hyaluronic acid is an important humidificating component in the dermis of the skin and has excellent viscosity and elasticity, it is an ideal filler and is usually used in cosmetic products and plastic surgery. Hyaluronic acid is a glycosaminoglycan containing no sulfur, the basic structure of which is a large polysaccharide consisting of two sugar units, D-glucuronic acid and D-N-acetylglucosamine, and has a chemical formula of the following formula (I):

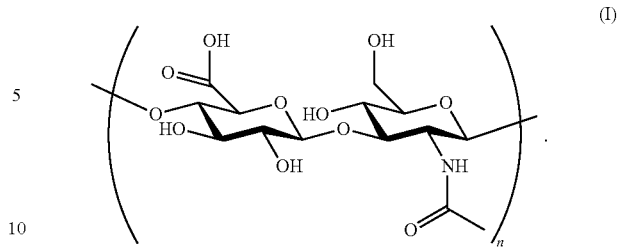

There is no a particular limit for hyaluronic acid used in the pharmaceutical composition of the present invention. Nevertheless, hyaluronic acid, as component (a) in the pharmaceutical composition of the present invention, preferably has an average molecular weight ranging from about 300,000 to about 6,000,000 Dalton, and more preferably has an average molecular weight ranging from about 500,000 to about 3,000,000 Dalton.

Component (b) in the pharmaceutical composition of the present invention is a 3-hydroxy-3-methylglutaryl-coenzyme A (HMG-CoA) reductase inhibitor (hereinafter referred to as "HMG-CoA" reductase inhibitor), comprising a kind of agents for reducing blood lipid called "statins." The statins comprise the compounds listed in the following Table 1.

TABLE 1

| Name | Formula | Commercial Name |
|---|---|---|
| Atorvastatin | *(structure shown)* | Lipitor or Torvast |
| Cerivastatin | *(structure shown)* | Lipobay or Baycol |
| Fluvastatin | *(structure shown)* | Lescol or Lescol XL |

TABLE 1-continued
| Name | Formula | Commercial Name |
|---|---|---|
| Lovastatin | 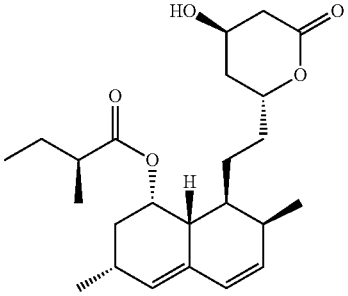 [SMILES: CC[C@H](C)C(=O)O[C@H]1C[C@@H](C)C=C2C=C[C@H](C)[C@H](CC[C@@H]3C[C@@H](O)CC(=O)O3)[C@H]21] | Mevacor, Altocor, or Altoprev |
| Mevastatin | 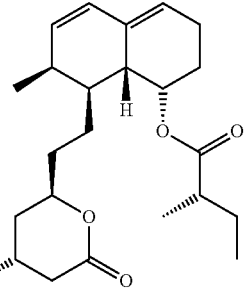 | None |
| Pitavastatin | 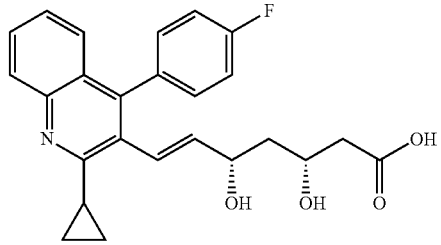 [SMILES: O=C(O)C[C@H](O)C[C@H](O)/C=C/c1c(C2CC2)nc2ccccc2c1-c1ccc(F)cc1] | Livalo or Pitava |
| Pravastatin | 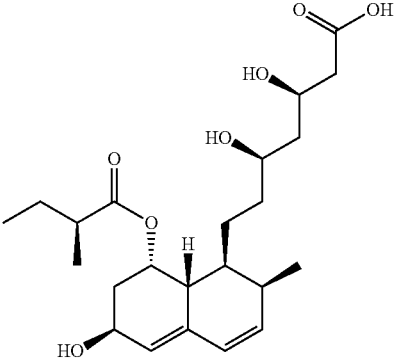 [SMILES: CC[C@H](C)C(=O)O[C@H]1C[C@H](O)C=C2C=C[C@H](C)[C@H](CC[C@@H](O)C[C@@H](O)CC(=O)O)[C@H]21] | Pravachol, Selektine, or Lipostat |
| Rosuvastatin | 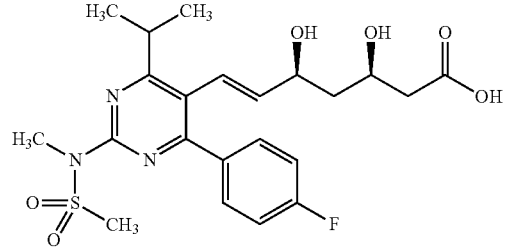 [SMILES: CC(C)c1nc(N(C)S(C)(=O)=O)nc(-c2ccc(F)cc2)c1/C=C/[C@@H](O)C[C@@H](O)CC(=O)O] | Crestor |

TABLE 1-continued

| Name | Formula | Commercial Name |
| --- | --- | --- |
| Simvastatin | | Zocor or Lipex |

Thus, HMG-CoA reductase inhibitors suitable as component (b) in the pharmaceutical composition of the present invention may be selected from a group consisting of Atorvastatin, Cerivastatin, Fluvastatin, Lovastatin, Mevastatin, Pitavastatin, Pravastatin, Rosuvastatin, Simvastatin, and combinations thereof. Component (b) is preferably Lovastatin. As shown in the following examples, although individually using an HMG-CoA reductase inhibitor may exacerbate inflammation, if using an HMG-CoA reductase inhibitor together with hyaluronic acid, surprisingly, the anti-inflammation effect of hyaluronic acid may be enhanced.

In the pharmaceutical composition of the present invention, there is no a particular limit for the content ratio of component (a) to component (b). Generally, the content of component (a) is about 80 wt % to about 99.9 wt %, and the content of component (b) is about 0.1 wt % to about 20 wt %, based on the total weight of components (a) and (b). Preferably, the content of component (a) is about 85 wt % to about 99.5 wt %, and the content of component (b) is about 0.5 wt % to about 15 wt %, based on the total weight of components (a) and (b).

The pharmaceutical composition of the present invention can be used in veterinary and human medicine, and may be in any forms and administrated in any appropriate ways. For example, but not limited to, the pharmaceutical composition can be administrated by oral administration, and subcutaneous, intravenous, or intra-articular injection, etc. A pharmaceutically acceptable carrier as component (c) may be contained in the pharmaceutical composition of the present invention, depending on the administration form or application of the pharmaceutical composition.

Taking a medicament suitable for the oral administration as an example, pharmaceutically acceptable carriers that will not adversely affect the activity of hyaluronic acid and HMG-CoA reductase inhibitors may be incorporated in the pharmaceutical composition of the present invention, for example, a solvent, an oily solvent, a thinner, a stabilizer, an absorption retarder, a disintegrant, an emulsifier, an anti-oxidant, a binder, a lubricant, a moisture absorbent, or the like. For example, the solvent may be selected from a group consisting of water and saccharose solutions; the thinner may be selected from a group consisting of lactose, starch, and microcrystalline cellulose; the absorption retarder may be selected from a group consisting of chitosan and glycosaminoglycans; the lubricant may be magnesium carbonate; the oily solvent may be selected from a group consisting of vegetable oils and animal oils, such as olive oil, sunflower oil, cod-liver oil, etc. By using any suitable conventional processes, the composition of the present invention may be formulated into a form suitable for oral administration, for example, into a form of tablets, capsules, granules, pulvis, fluid extracts, solutions, syrups, suspensions, emulsions, tinctures, and so on.

When a medicament form suitable for subcutaneous, intravenous, or intra-articular injection is desired, one or more components, such as a isotonic solution, a salt buffer solution (e.g., a phosphate buffer solution or a citrate buffer solution), a solubilizer, an emulsifier, other carriers, or the like, may be incorporated in the pharmaceutical composition of the present invention to prepare an intravenous fluid injection, an intravenous emulsion injection, a dry powder injection, a suspension injection, a dry powder suspension injection, or the like. Solvents that may be adopted include, for instance, water, normal saline, alcohols (e.g., ethylene glycol, propanol, glycerin, etc), sugar solutions (e.g., glucose solutions or mannose solutions), or combinations thereof.

The pharmaceutical composition of the present invention may optionally further comprise additives such as a flavoring agent, a color toner, a coloring agent, and the like to improve the mouth feel and visual experience when the resulting medicament is taken; also, a preservative, an antiseptic, an antimicrobial (such as benzyl alcohol), an antimycotic, or the like may be added at a reasonable amount to improve the storability of the resulting medicament.

Furthermore, one or more other active components may be optionally incorporated in the pharmaceutical composition of the present invention to further enhance the efficacy of the composition or to increase flexibility for manufacturing formulations. For example, one or more of the following active components may be contained in the pharmaceutical composition of the present invention: steroidal anti-inflammation agents, non-steroidal anti-inflammation agents, and glucosamine as well as other active components, provided that the other active component(s) will not adversely affect the efficacy of hyaluronic acid and HMG-CoA reductase inhibitors.

Because the pharmaceutical composition of the present invention may inhibit the transient inflammatory reactions caused by hyaluronic acid and promote the anti-inflammation effect of hyaluronic acid, it can be used for inhibiting inflammation, especially can be used for inhibiting arthritis, including osteoarthritis (degenerative arthritis), rheumatoid arthritis (RA), gouty arthritis, bacterial arthritis, ankylosing spondylitis, lupus erythmatosus, etc. Preferably, the pharmaceutical composition is useful in inhibiting osteoarthritis and rheumatoid arthritis. In one embodiment, the pharmaceutical composition of the present invention is made in a form of an injection for the intra-articular injection therapy.

Compared with the conventional hyaluronic acid formulations, which cannot efficiently treat rheumatoid arthritis, one of the advantages of the pharmaceutical composition of the present invention is that the composition of the present invention can provide an excellent effect of inhibiting rheumatoid arthritis, and thus it especially can be used in the treatment of rheumatoid arthritis. Besides, the present invention is different from the known combination of hyaluronic acid and MTX, which needs a complicated approach and use of polypeptides to form the conjugate to provide a desired anti-inflammation effect. In the pharmaceutical composition of the present invention, only a simple mix of mixing hyaluronic acid and an HMG-CoA reductase inhibitor is needed, and thus the present invention has advantages like easy preparation and mass production.

Because the pharmaceutical composition of the present invention can improve the drawbacks of the conventional hyaluronic acid formulations, it also can be used in any known applications of hyaluronic acid, not limited to anti-arthritis. For example, the composition of the present invention can be applied in cosmetic products or plastic surgery; for instance, it can be added into skin care products or facial hyaluronic acid injections.

The present invention also provides a method for inhibiting inflammation in a mammal, comprising administrating to the mammal an effective amount of a composition comprising hyaluronic acid and an HMG-CoA reductase inhibitor. The average molecular weight of hyaluronic acid, the species of the HMG-CoA reductase inhibitor, and the content ratio of hyaluronic acid and the HMG-CoA reductase inhibitor are defined as the above. In one embodiment of the present invention, the pharmaceutical composition of the present invention, in a form of an injection, is injected into the joint of a subject to achieve the effect of treating arthritis.

Depending on the demands of the subject who receives the administration, the pharmaceutical composition of the present invention may be administrated with different frequencies, such as once every day, several times every day, once every several days, etc. For example, when used in a human body for treating rheumatoid arthritis, the composition may be administrated in an amount of, based on components (a) and (b), about 25 mg/kg-body weight per day to about 50 mg/kg-body weight per day. Herein, the unit "mg/kg-body weight" refers to an amount of the composition to be administrated per kg of body weight. However, for patients with acute conditions (e.g., for patients with gout), the amount of administration may be increased by several or several tens of times depending on practical conditions.

Hereinafter, the present invention will be further illustrated with reference to the following examples. However, these examples are only provided for illustration purposes, but not to limit the scope of the present invention.

PREPARATION EXAMPLE

Preparation of a Hyaluronic Acid Injection Solution for Intra-Articular Administration In a hyaluronic acid injector (purchased from Ocean Bright, Co., Ltd., Taiwan), 1 ml of an isotonic solution was added, and the solution contained 5 to 20 mg hyaluronic acid (the average molecular weight: 600,000 to 800,000 Dalton; purchased from Ocean Bright, Co., Ltd., Taiwan) and 0.5 to 1.2 mg of an HMG-CoA reductase inhibitor (lovastatin, M2147, purchased from Sigma-Aldrich Co.) as major components, and 5 to 20 mg of NaCl, $NaHSO_4$, $NaH_2SO_4$, and water for injection was added into the solution as excipients, thereby preparing a hyaluronic acid injection solution for intra-articular administration.

EXAMPLE 1

Cell Assay for the Hyaluronic Acid Injection Solution

Experiment A. Cell Culture

Fibroblast-like synoviocytes (FLS) from seven patients with rheumatoid arthritis (RA) were collected and incubated. First, the joint synovia from the patients were cut into small pieces and suspended in a DMEM medium (Dulbecco modified eagle's medium, comprising 1.5 g/L sodium bicarbonate (S6297, Sigma-Aldrich Co. St Louis, Mo., USA), 1% penicillin-streptomycin-neomycin (P4083, Sigma-Aldrich Co.), and 10% fetal bovine serum (04-001-1A, Biological Industries, Grand Island, N.Y., USA)), and were incubated in the environment under 37° C., 5% $CO_2$ for three days.

The non-adherent cells were washed out with a phosphate buffer solution (PBS), the medium was refreshed, and the retained adherent cells were cultivated for two weeks. The above procedure was repeated three to six times, and the retained cells were FLS, which were used in the following experiments.

Experiment B. Cell Treatment

The FLS prepared from Experiment A were incubated in a medium containing no serum for 24 hours until the cells grew to a subconfluence state, and the cells were incubated in a DMEM medium containing 10% fetal bovine serum. The cells were then divided into four groups: 1) a control group, in which the cells were not treated or stimulated; 2) an HA group, in which the cells were treated with only hyaluronic acid (the average molecular weight: 600,000 to 800,000 Dalton) for 24 hours; 3) an HMG-CoA reductase inhibitor group, in which the cells were treated with only an HMG-CoA reductase inhibitor (lovastatin, M2147, Sigma-Aldrich Co.) for 24 hours; and 4) a mixture group, in which 100 μg hyaluronic acid (the average molecular weight: 600,000 to 800,000 Dalton) and 5 micro-mole of an HMG-CoA reductase inhibitor (lovastatin) were mixed in a solution (1 ml), and the cells were treated with the resultant mixture for 24 hours.

Then, the cells in the above four groups were collected and centrifuged respectively, and the supernatants were collected to conduct the following assays.

Experiment C. Quantification of RA-Related Proteins

The concentrations of two RA-related factors, TNF-α (the standard sample was purchased from eBioscience, Ltd., 88-7340) and IL-8 (the standard sample was purchased from R&D systems, Inc., USA, DY208), in the supernatants collected from Experiment B were measured using a sandwich binding protein assay kit or sandwich ELISA kits (purchased from eBioscience, Ltd. and R&D systems, Inc.) according to the manufacturer's manual and standard curves to observe the expression level of the factors, thereby determining the inflammation condition of the cells. Each sample was analyzed twice, and an ELISA reader (Sunrise Remote, TECAN) was used to conduct the measurement. The results are shown in Tables 2 and 3 and FIGS. 1 and 2.

TABLE 2

TNF-α concentration

| Group | Control group | HA group | HMG-CoA reductase inhibitor group | Mixture group |
|---|---|---|---|---|
| Average concentration (pg/ml) | 347.00 | 296.46 | 355.07 | 260.28 |

TABLE 3

IL-8 concentration

| Group | Control group | HA group | HMG-CoA reductase inhibitor group | Mixture group |
|---|---|---|---|---|
| Average concentration (pg/ml) | 736.00 | 353.40 | 703.94 | 347.76 |

[Experiment Results]

Figure 2:
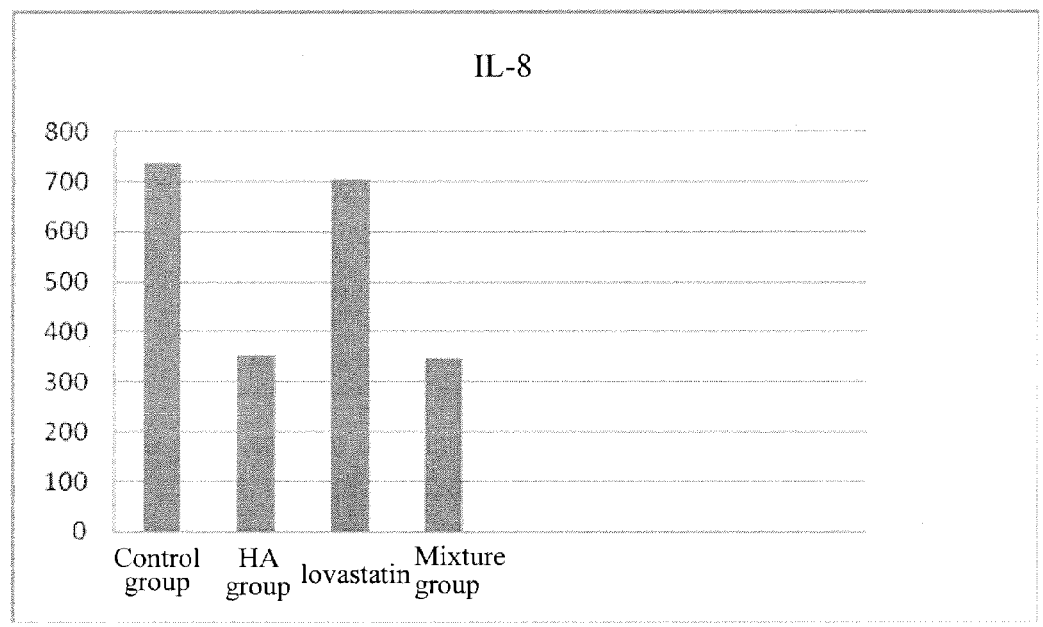
FIG. 2 is a statistical bar graph showing the expression level of the inflammatory mediator IL-8 in the FLS.

Tables 2 and 3 and FIGS. 1 and 2 show that the articular cells FLS from the patients with RA secreted a large amount of inflammatory mediators TNF-α and IL-8, indicating that the inflammation level was severe (as shown in the control group). However, when the cells were treated with hyaluronic acid only, the inflammation level was lowered. In addition, if the HMG-CoA reductase inhibitor and hyaluronic acid were combined to treat the cells, the effect of inhibiting the inflammation from hyaluronic acid was further enhanced (as shown in the mixture group).

As a result, the above examples indicate that, compared with the treatment using hyaluronic acid only, the combination of the HMG-CoA reductase inhibitor and hyaluronic acid is more effective to lower the concentration of the inflammatory mediators TNF-α and IL-8. In other words, combining the HMG-CoA reductase inhibitor and hyaluronic acid has a better anti-inflammation effect than using hyaluronic acid only. This result proves that the pharmaceutical composition of the present invention may enhance the anti-inflammation effect of hyaluronic acid, and has a better effect of inhibiting the inflammation for rheumatoid arthritis. Furthermmore, the result also proves that the pharmaceutical composition of the present invention may inhibit the transient inflammatory reactions caused by hyaluronic acid.

The above disclosure is related to the detailed technical contents and inventive features thereof. People skilled in this field may proceed with a variety of modifications and The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for inhibiting arthritis in a mammal in need thereof, comprising administrating to the mammal an effective amount of a mixture comprising (a) hyaluronic acid and (b) a 3-hydroxy-3-methylglutaryl-coenzyme A (HMG-CoA) reductase inhibitor, wherein the mixture comprises about 85 wt % to about 99.5 wt % of hyaluronic acid and about 0.5 wt % to about 15 wt % of the HMG-CoA reductase inhibitor, based on the total weight of hyaluronic acid and the HMG-CoA reductase inhibitor, and wherein the mixture is administered by intra-articular injection.

2. The method as claimed in claim 1, wherein the hyaluronic acid has an average molecular weight ranging from about 300,000 to about 6,000,000 Dalton.

3. The method as claimed in claim 2, wherein the hyaluronic acid has an average molecular weight ranging from about 500,000 to about 3,000,000 Dalton.

4. The method as claimed in claim 1, wherein the HMG-CoA reductase inhibitor is selected from a group consisting of Atorvastatin, Cerivastatin, Fluvastatin, Lovastatin, Mevastatin, Pitavastatin, Pravastatin, Rosuvastatin, Simvastatin, and combinations thereof.

5. The method as claimed in claim 4, wherein the HMG-CoA reductase inhibitor is Lovastatin.

6. The method as claimed in claim 1, wherein the arthritis is selected from the group consisting of osteoarthritis, rheumatoid arthritis and gouty arthritis.

7. The method as claimed in claim 6, wherein the arthritis is rheumatoid arthritis.

8. A method for inhibiting arthritis in a mammal in need thereof, comprising administrating to the mammal an effective amount of a mixture comprising (a) hyaluronic acid and (b) a 3-hydroxy-3-methylglutaryl-coenzyme A (HMG-CoA) reductase inhibitor, wherein the mixture comprises about 85 wt % to about 99.5 wt % of hyaluronic acid and about 0.5 wt % to about 15 wt % of the HMG-CoA reductase inhibitor, based on the total weight of hyaluronic acid and the HMG-CoA reductase inhibitor.

9. The method as claimed in claim 8, wherein the hyaluronic acid has an average molecular weight ranging from about 300,000 to about 6,000,000 Dalton.

10. The method as claimed in claim 9, wherein the hyaluronic acid has an average molecular weight ranging from about 500,000 to about 3,000,000 Dalton.

11. The method as claimed in claim 8, wherein the HMG-CoA reductase inhibitor is selected from a group consisting of Atorvastatin, Cerivastatin, Fluvastatin, Lovastatin, Mevastatin, Pitavastatin, Pravastatin, Rosuvastatin, Simvastatin, and combinations thereof.

12. The method as claimed in claim 11, wherein the HMG-CoA reductase inhibitor is Lovastatin.

13. The method as claimed in claim 8, wherein the arthritis is selected from the group consisting of osteoarthritis, rheumatoid arthritis, and gouty arthritis.

14. The method as claimed in claim 13, wherein the arthritis is rheumatoid arthritis.

* * * * *